US012582189B2

(12) United States Patent
Weber

(10) Patent No.: US 12,582,189 B2
(45) Date of Patent: Mar. 24, 2026

(54) HELMET GOGGLE DESIGNED FOR ON-ROAD AND OFF-ROAD USE

(71) Applicant: 6D Helmets, LLC, Brea, CA (US)

(72) Inventor: Robert S. Weber, Fullerton, CA (US)

(73) Assignee: 6D Helmets, LLC, Brea, CA (US)

( * ) Notice: Subject to any disclaimer, the term of this patent is extended or adjusted under 35 U.S.C. 154(b) by 0 days.

(21) Appl. No.: 17/744,658

(22) Filed: May 14, 2022

(65) Prior Publication Data

US 2022/0361619 A1 Nov. 17, 2022

Related U.S. Application Data

(60) Provisional application No. 63/189,076, filed on May 15, 2021.

(51) Int. Cl.
*A42B 3/22* (2006.01)
*A42B 3/18* (2006.01)
*A61F 9/02* (2006.01)

(52) U.S. Cl.
CPC .............. *A42B 3/221* (2013.01); *A42B 3/185* (2013.01); *A61F 9/027* (2013.01); *A61F 9/029* (2013.01)

(58) Field of Classification Search
CPC ......... A42B 3/185; A42B 3/042; A42B 3/221; A61F 9/027
See application file for complete search history.

(56) References Cited

U.S. PATENT DOCUMENTS 5,157,794 A 10/1992 Kamata
6,076,196 A * 6/2000 Masumoto .............. A61F 9/028
2/452

(Continued)

FOREIGN PATENT DOCUMENTS

DE 202004001735 U1 7/2004
KR 20020080280 10/2002

OTHER PUBLICATIONS

European Patent Office; Patent Translate; Krauter, Manfred; Air deflector helmet with air deflector and goggles for it; German Patent DE 202004001735 U1; Jul. 15, 2004.

(Continued)

*Primary Examiner* — Khoa D Huynh
*Assistant Examiner* — Erick I Lopez
(74) *Attorney, Agent, or Firm* — E. Victor Indiano; Indiano Law Group, LLC

(57) ABSTRACT

A protective helmet for use with motorsports and cycling activities has a head receiving helmet body that includes a head receiving interior, and an exterior having a front surface, a rear surface, and a perimetral lip for defining a forward-facing aperture. A transparent shield member is engageable with the helmet body and is configured to be placeable adjacent to the forward-facing aperture of the helmet body. The shield member includes a perimetral edge that is sized and configured for engaging the perimetral lip of the helmet body. A strap is coupled to the shield and is configured to engage the rear surface of the helmet body. The engagement of the perimetral edge of the shield member with the perimetral lip of the helmet body enables an increasing force exerted against the shield to be exerted against the helmet, rather than directly against the user's face, and resists the intrusion of dust into the interior of the helmet.

23 Claims, 15 Drawing Sheets

(56)                    References Cited

U.S. PATENT DOCUMENTS

| | | | |
|---|---|---|---|
| 6,742,192 B1 * | 6/2004 | Song ........................ | A42B 3/24 |
| | | | 2/424 |
| 9,848,667 B2 | 12/2017 | Brace et al. | |
| 2011/0016595 A1 * | 1/2011 | Brace ..................... | A42B 3/225 |
| | | | 29/527.1 |
| 2012/0117717 A1 * | 5/2012 | McGinn ................. | A42B 3/326 |
| | | | 2/243.1 |
| 2014/0196199 A1 * | 7/2014 | Huffman .................. | A42B 3/20 |
| | | | 2/421 |
| 2019/0000674 A1 | 1/2019 | Bouchard Fortin et al. | |
| 2020/0142218 A1 * | 5/2020 | McNeal .................. | A61F 9/029 |

OTHER PUBLICATIONS

Google Patent Translate; Lee, Kwang-Woo; Motorcycle helmet provided with glare shielding glass; Korean Patent KR 20020080280; Oct. 23, 2002.
Commissioner for Patents; International Search Report PCT/US2022/029352 issued Aug. 10, 2022.

* cited by examiner

HELMET GOGGLE DESIGNED FOR ON-ROAD AND OFF-ROAD USE

PRIORITY STATEMENT

The instant application claims benefit of priority to Robert Weber U.S. Provisional Patent Application No. 63/189,076 that was filed on 15 May 2021 for a HELMET GOGGLE DESIGNED FOR ON-ROAD AND OFF-ROAD USE, which patent application is incorporated in its entirety by reference herein.

TECHNICAL FIELD OF THE INVENTION

The present invention relates to protective gear and, more particularly, to helmet-type protective gear including face and eye protection.

BACKGROUND OF INVENTION

Sports that involve movement and potential contact, often involve the use of helmets to help protect the head of the participant in the activity. Helmets come in a wide variety of designs and styles. The design of a helmet is usually dictated by the activity with which the helmet is used. The designs of different activity-related helmets, such as hockey helmets, football helmets, lacrosse helmets, skiing helmets, auto racing helmets, and motorcycle helmets are very different, as the activities are different and the risks and natures of the contacts that are typical to the activity are different.

Different types of helmets may exist even within a particular type of activity, such as baseball, where the helmet that a catcher wears is different than the helmet that a batter wears. Likewise, helmets designed for use with dirt bikes are often different than helmets that are designed for use with road bikes.

One activity factor that tends to require a difference in motorcycle, bicycle, and motorsports helmet design is whether the activity is performed on a road surface or an off-road surface. Typically, motorsport activities that occur on road surfaces, such as street motorcycles and go-karts, are usually conducted over a longer period of time and conducted in a relatively dust-free environment.

In contrast, activities that are conducted in an off-road environment, such as off-road motorcycle and all-terrain vehicle riding are often conducted over shorter intervals and are conducted in relatively more dusty and dirty environments. For this reason, street use helmets and off-road helmets are designed differently.

A large variety of different types of helmet types exist for use in motorcycles and off-road vehicles including full-face helmets. Examples of full-face helmets designed primarily for on street use are the Bell Race Star Flex DLX and the Speed and Strength SS4100 Spikes Gray Modular Helmet; and the Icon Airflight Helmet. All three of these helmets are available at www.jpcycles.com.

Examples of off-road motorcycle helmets include the Bell Moto 9 Flex helmet that is available from www.motosport.com; the Fox V3 Helmet, available from www.foxracing.com; and goggles that are usable with the aforementioned dirt bike motorcycle helmets such as the Oakely Airbrake MX Goggle that is available at www.oakley.com, and Fox Racing Vue Pyre Goggles that are available at www.foxracing.com.

Typical full-face helmet include a crown portion that extends over the top of the user's head, first and second side portions that extend along the side of the user's head, a rear portion extending down to about the base of the skull, and a chin bar portion that extends forwardly along the cheeks and front of the user's face. A front-facing aperture is formed that is generally co-extensive with the eyes, temple, and nose of the user.

To protect the user's eyes, an eye protection device extends either over or within this frontal aperture. A primary difference between an on-road and an off-road helmet is the nature of this eye protection.

In street helmets, this eye protection usually takes the form of a shield member that is pivotably coupled to the helmet at a point that is generally co-extensive with the ear of the user. The shield member has an edge portion which engages the lip of the helmet that defines the frontal aperture. The shield is movable between a down position, wherein it is in front of the user's face to an up position where it is disposed adjacent to the crown of the helmet, to thereby allow air into the helmet.

A shield is used with street helmets because it addresses the issues that are typically encountered by street bike users.

Street bike users typically travel at a higher rate of speed than off-road riders. The wind at these higher speeds exerts a force against the shield that is in a direction that exerts a front-to-rear force on the front of the user's face, if the shield was in direct contact with the face. In order to reduce this pressure on the user's face, the shield rests on the lip of the helmet so that the rearwardly speed induced wind force on the shield is exerted against the lip of the helmet rather than directly against the user's face.

By doing this, the user is more comfortable than she would be if the user encountered this wind-induced pressure directly against her face. Additionally, the eyes and face are protected from bugs, road matter, or other debris that are encountered while riding at speeds.

Additionally, there is typically a significant amount of space between the lower edge of the helmet and the user's chin, shoulder, and back of the head. This space provides an area into which air can flow into the interior of the helmet to help cool the user. Because of the speed at which the user is traveling, sufficient air flow is usually provided to help keep the user cool under most conditions. As the street rider is normally not riding in an overly dusty environment, the fact that air can get into a user's helmet does not necessarily cause dust-related irritation to the user.

In contrast, off-road motorcycle helmets often are used with goggles rather than shields. Goggles are employed with off-road helmets because most goggles have a sealing mechanism such as a gasket which extends around the rearwardly facing perimeter of the goggle and engages the user's face. This perimetral seal helps to prevent dust from encountering the user's eyes. Road and trail dust typically is comprised of small particulates. A typical road dust particulate may have an average size of about 10 microns, although dust particulates as small as 2 microns or less are not uncommon, as are large particulates. See, Guan Zhao, Yenyu Chen, Philip K. Hopke, Thomas M. Holsen, &Suresh Dhaniyala, "Characteristics of Traffic-Induced Fugitive Dust from Unpaved Roads" *Aerosol Science and Technology Volume* 51, 2017—Issue 11

The goggles usually include an elastic band, that extends from one side of the goggles to the other side of the goggles and is placed at about ear level around the back of the helmet to hold the goggles onto the user's face.

A primary advantage of the user of goggles is that the gasket seal helps to keep dust from engaging the user's eyes. However, a drawback of the use of goggles is that the band and the seal exert pressure against the front of the user's face. However, this pressure is not at the level that one would normally encounter with a street bike, since the speed at which off-road persons ride is typically much lower than that of street bikes, and is often for a lesser time period. Viewed another way, the enhanced ability of the goggles to keep out dust more than compensates for the inconvenience of the pressure exerted on the user's face.

Recently, there has been a surge in motorcycle riders engaging in an activity that is referred to as "adventure touring" or "dual sport riding". Generally, these activities refer to a motorcycling activity where a motorcycle rider's journey will include time and miles spent on a street surface along with time and miles spent off-road. On a typical adventure, the user will leave his home and travel on the streets to an off-road venue or trail system. At the off-road venue, the user may then ride his motorcycle on off-road trails for a period of time before returning to the street and riding home. In many cases, the user may ride many miles on-road before going to the off-road venue.

This activity has become popular enough so that a new category of motorcycles exist called adventure touring motorcycles. Generally, adventure touring motorcycles are heavier and have larger engines than a typical dirt bike, but are smaller and lighter than a typical street bike.

Unfortunately, neither the street helmet nor the off-road helmet works well for such adventure touring. In particular, a street helmet will serve the rider well while he is on a street surface. However, because it is designed to facilitate cooling of the user by allowing air to enter the user's head space, the street helmet does not work well off-road because it allows too much dust into the user's head space where it can interfere with the user's vision by causing the user to get dust in his eyes.

Similarly, the off-road motorcycle helmet does not work well on the street. Although the engagement between the perimetral gasket of the goggles does a good job of preventing dust from infiltrating the area of the user's eyes, its overall design is a compromise for use on the street. Further, the use of goggles on a road trip can be uncomfortable and fatiguing. The constant wind pressure that the goggles place against the user's face, combined with the elastic band holding the goggles in place, make this setup undesirable for street use. Additionally, the traditional goggle is much noisier than a traditional style shield when speeds increase to common highway speeds causing additional rider fatigue and/or discomfort.

This pressure against the user's face is exacerbated by the fact that riders typically travel at a much higher rate of speed on a street surface than they do off-road. This increased speed increases the air pressure that is exerted on the goggles by the force of the wind while the motorcycle is traveling at speed. Therefore, this air pressure causes the goggles to press uncomfortably against the user's face, thus causing discomfort when the user employs goggles while riding on the street.

One object of the present invention is to provide a helmet and goggle solution that has desirable characteristics when used both on road surfaces and when used off-road.

SUMMARY OF THE INVENTION

In accordance with the present invention, a protective helmet is provided for use with motorsports and cycling activities. The helmet, comprises a head receiving helmet body that includes a head receiving interior, and an exterior having a front surface, a rear surface, and a perimetral lip for defining a forward-facing aperture. A transport shield member is engageable with the, helmet body and is configured to be placeable adjacent to the forward-facing aperture of the helmet body. The shield member includes a front surface, a rear surface, and a perimetral edge having a top portion, a bottom portion, a first side portion, and a second side portion. A perimetral edge is sized and configured for engaging the perimetral lip of the helmet body.

A strap has a first end, a second end, and a middle portion that extends between the first and second ends. The first end is coupled to the first side portion of the transparent shield and the second end is coupled to the second side portion of the transparent shield. The middle portion is configured to engage the rear surface of the helmet body.

The engagement of the perimetral edge of the shield member with the perimetral lip of the helmet body enables an increasing force exerted against the shield to be exerted against the helmet, rather than directly against the user's face.

In a preferred embodiment, the helmet includes a sealing member that is cooperatively positioned with the helmet body and user's face to help reduce the intrusion of particulates, such as road dust, into an area adjacent to the user's eyes. In a most preferred embodiment, the helmet shield member includes a transparent lens having a perimetral lens edge. The sealing member includes a first portion that, is placeable against the front surface of the shield member, a second portion placeable against the rear surface of the shield member, and a middle portion containing a groove that is disposed between the first and second portions. The groove is sized and configured for receiving the perimetral lens edge, and the sealing member preferably extends around each of the upper portion, lower portion, first side portion, and second side portion.

In another aspect of the instant invention, a shield is provided for use with a protective motor sports or cycling helmet for use with motor sports and cycling that includes a head receiving interior, and an exterior having a front surface, a rear surface, and a perimetral lip for defining a forward facing aperture.

The shield comprises a transparent shield member engageable with the helmet body and configured to be placeable adjacent to the forward facing aperture of the helmet body. The shield member includes a front surface, a rear surface, and a perimetral edge having a top portion, a bottom portion, a first side portion and a second side portion. The perimetral edge is sized and configured for engaging the perimetral lip of the helmet body.

A strap is provided that has a first end, a second end, and a middle portion extending between the first and second ends. The first end is coupled to the first side portion of the transparent shield, the second end is coupled to the second side portion of the transparent shield and the middle portion is configured to engage the rear surface of the helmet body. The engagement of the perimetral edge of the shield member with the perimetral lip of the helmet body enables an increasing force exerted against the shield to be exerted against the helmet rather than directly against the user's face.

One feature of the present invention is that a helmet goggle is provided that can provide the dust-avoidance features of a traditional goggle system without inducing the undue pressure on the user's face when ridden on the street.

Another feature of the present invention is that the strap-engagement between the shield and helmet provides a shield that is easily removable from the helmet when the user wishes to employ the helmet in a shieldless configuration.

These and other features and advantages of the present invention will become apparent to those skilled in the art upon a review of the figures and written description presented below, which represent the presently perceived best mode of carrying out the invention.

DETAILED DESCRIPTION

Figure 1:
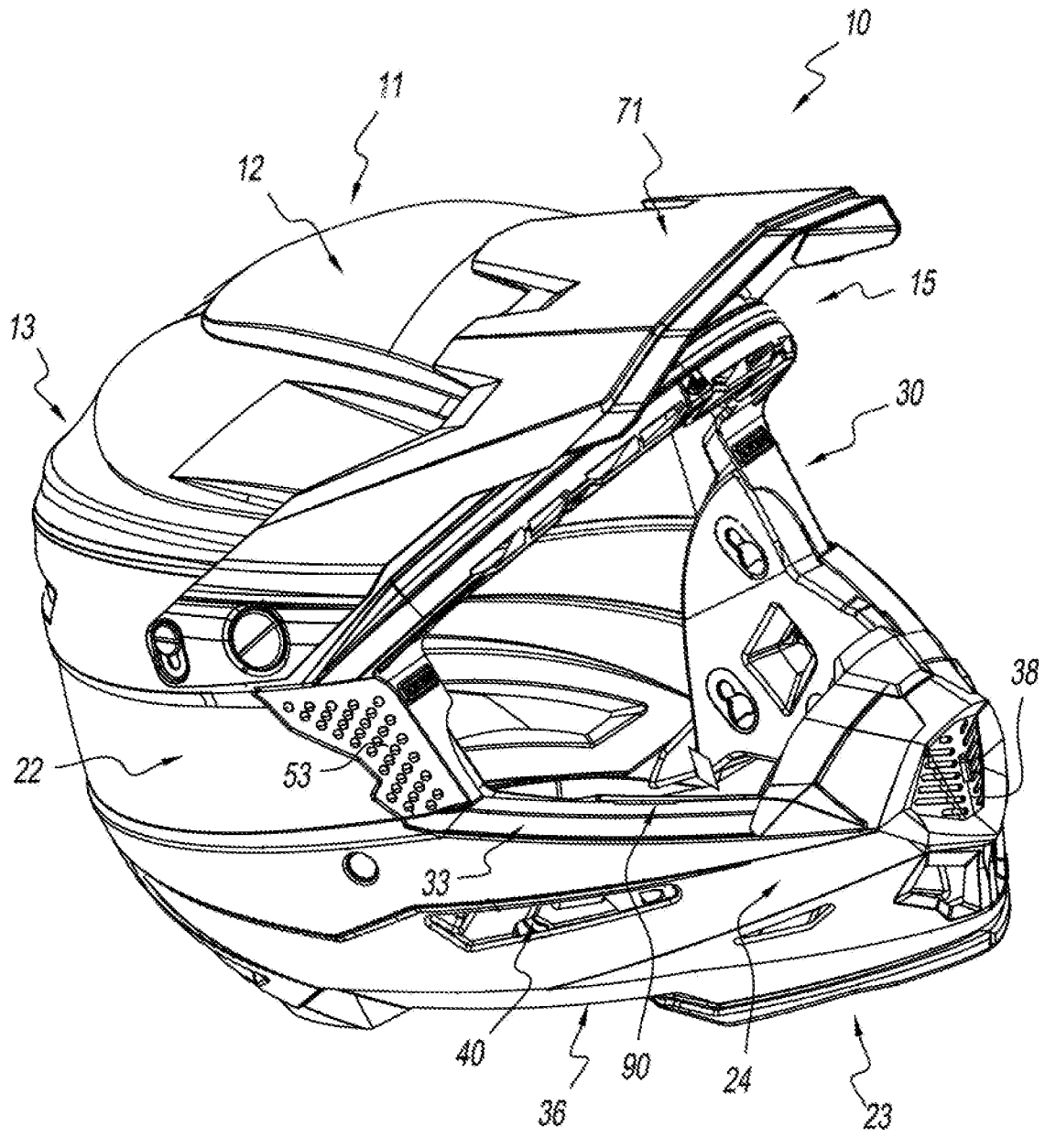
FIG. 1 is a right-side perspective view of a full-face motorcycle helmet of the present invention, to which the goggle/shield of the present invention can be coupled.
Figure 2:
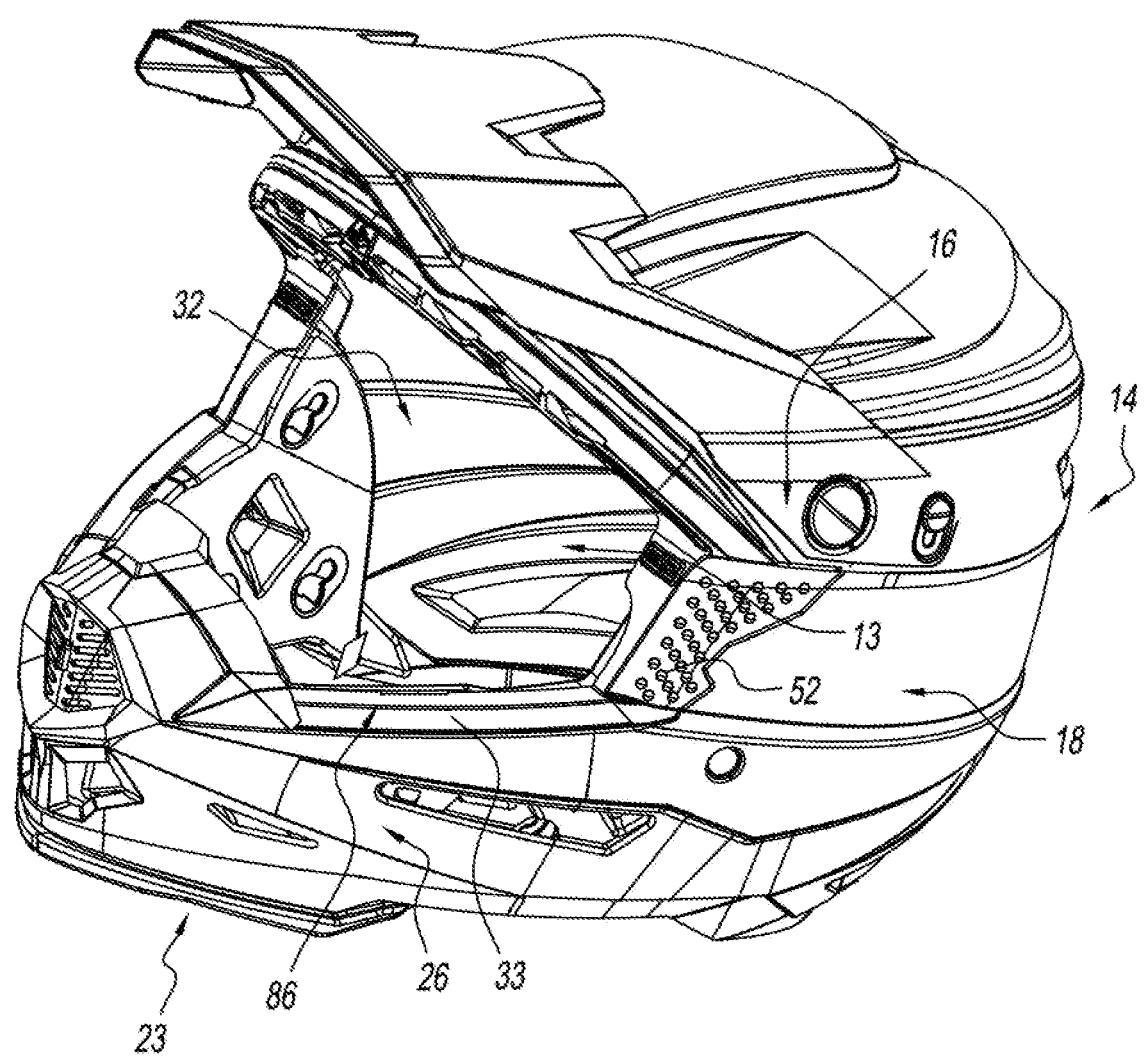
FIG. 2 is a left-side frontal perspective view of the motorcycle helmet of FIG. 1.
Figures 3, 4:
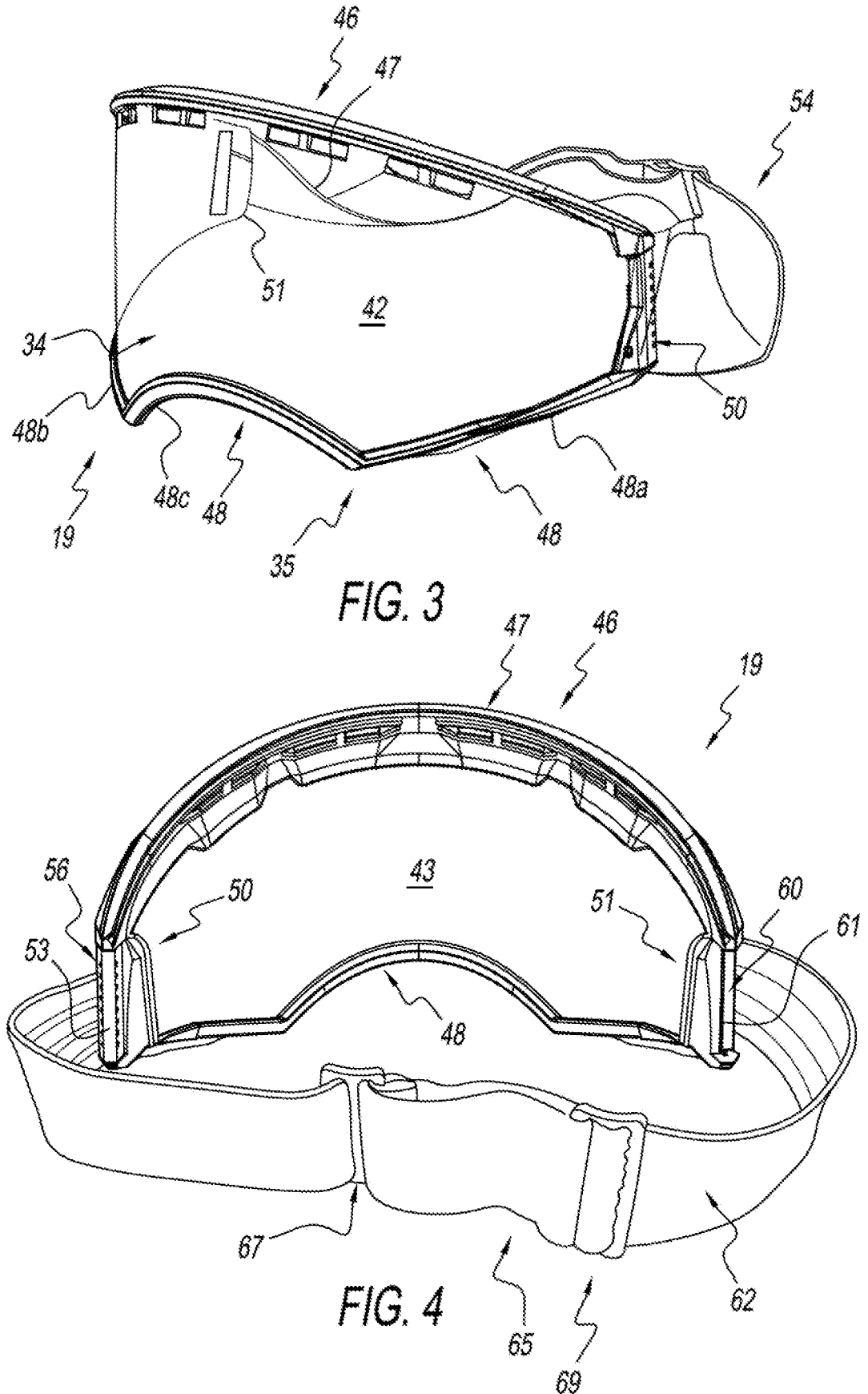
FIG. 3 is a left-front perspective view of the goggle of the present invention.
FIG. 4 is a rear view of the goggle of the present invention, showing the inside surface of the shield member.

The description that follows describes, illustrates and exemplifies one or more particular embodiments of the present invention in accordance with its principles. This description is not provided to limit the invention to the embodiment or embodiments described herein, but rather to explain and teach the principles of the invention in such a way to enable one of ordinary skill in the art to understand these principles and, with that understanding, be able to apply them to practice not only the embodiment or embodiments described herein, but also other embodiments that may come to mind in accordance with these principles.

The scope of the present invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing reference numbers, such as, for example, in cases where such labeling facilitates a clearer description. Additionally, the drawings set forth herein are not necessarily drawn to scale, and in some instances proportions may have been exaggerated to more clearly depict certain features. Such labeling and drawing practices do not necessarily implicate an underlying substantive purpose.

Furthermore, certain views are side views which depict only one side of the device (or one set of components of a multi set array of components), but it will be understood that the opposite side and other component sets are preferably identical thereto. The present specification is intended to be taken as a whole and interpreted in accordance with the principles of the present invention as taught herein and understood by one of ordinary skill in the art.

A protective helmet 10 is provided for use with motorsports and cycling activities. The helmet 10 has a head receiving helmet body 11 that includes a head receiving interior 13, and an exterior 17 having a crown portion 12, a front surface 15, a rear surface 14, a left side portion 18, and a perimetral lip 33 for defining a forward-facing aperture 32 A transparent shield member 19 is engageable with the helmet body 11 and is configured to be placeable adjacent to the forward-facing aperture 32 of the helmet body 11. The shield member 19 includes a front surface 42, a rear surface 43, and a perimetral edge 46 having a top portion 47, a bottom portion 48, a first side portion 50, and a second side portion 51. The perimetral edge 46 is sized and configured for engaging the perimetral lip 33 of the helmet body 11.

A strap 54 having a first end 56, a second end 60 and a middle portion 62 that extends between the first 56 and second 60 ends. The first end 56 is coupled to the first side portion 50 of the transparent shield and the second end 60 is coupled to the second side portion 51 of the transparent shield. The middle portion 62 is configured to engage the rear surface 14 of the helmet body 10.

The engagement of the perimetral edge 46 of the shield member 19 with the perimetral lip 33 of the helmet body 10 enables an increasing force exerted against the shield member 19 to be exerted against the helmet 10, rather than directly against the user's face.

Many of the parts of the helmet are referenced with respect to the body part that it covers or is placed against. As such, the helmet 10 has a top or crown portion 12 that generally extends over the top of user's head, a rear surface portion 14 that is generally vertically disposed and extends over the back of the user's head and a brow portion 16. The, brow portion 16 comprises the front part of the crown portion 12 and is placed adjacent to user's forehead or brow.

The helmet 10 also includes a left side portion 16 that is disposed adjacent to the left side of the user's head, that extends generally forwardly as far as the user's ear and rearwardly until it merges into the rear portion 14. Similarly, a corresponding right side portion 22 of the helmet 10 is provided that is disposed adjacent to the right side of the user's head.

A chin bar 23 extends forwardly from the side portions 20 22. The chin bar 23 includes a right jaw portion 24 that extends along the user's right jaw and a left jaw portion 26 that extends along the user's left jaw. A chin portion 28 is disposed at the front of the helmet between the right 24 and left 26 jaw portions and is generally placed adjacent to the user's chin. A visor 71 may be attached to the crown portion.

A face portion 30 extends in a position at the front of the helmet adjacent to the user's face. The face portion 30 consists primarily of an aperture 32 that is defined by a perimetral lip 33 that extends along the upper edge of the chin portion 28, jaw portions 24, 26, front and side surfaces of the side portions, and the lower surface of the brow portion 16. A base edge 36 extends around the bottom of the helmet 10, and defines an aperture through which the user extends his head, to place his head into the interior 13 of the helmet.

A closeable chin vent 38 (sometimes called a nose vent) is disposed on the chin portion 28 of the helmet. The chin vent 38 is provided for enabling air to pass through from the outside of the helmet 10 to the interior 13 of the helmet to help cool the user's head and to provide fresh air for breathing. The chin vent 38 preferably includes a filter (not shown), to filter out particulates such as dust and water, to prevent these irritants from entering the interior of the helmet.

In the adventure touring helmet shown, the chin vent 38 is preferably adjustable between an opened position such that air can flow through it 38, and a closed position, wherein the flow of air through the vent 38 is restricted. This enables the user to open the vent 38 when riding on dirt, but close to the vent when the user is driving on the street or vise-versa. Preferably, the chin vent 38 is closeable so that the user is not overwhelmed by the flow of air flowing through the chin vent 38 at the high speeds typically employed on street surfaces.

In addition to the chin vent 38, jaw vents 40 are provided on each of the left and right jaw portions 26, 24 respectively which also may include filters for filtering out particulate matter and water. Of course, it is envisioned that some of the helmets with which the present invention is used will not have chin vents and/or jaw vents.

The forward portion of the left side portion 20 of the helmet includes a recessed left side shield seat surface 50 and the front portion of the helmet includes a right side shield seat surface 48 that is provided for receiving the right side of the shield 19. The purpose of the left and right side seats 50, 48 are to fixedly position the side of the shield 49 when the shield is engaged with the helmet 10 so that the shield 19 stays in its appropriate place, and does not slide upwardly, downwardly, or rotationally on the helmet 10. A large amount of protective padding is provided in the interior of the helmet 10 to capture the user's head, and to protect the user's head by cushioning it against blows and trauma that might occur if the user's head hits something, such as a road surface or another vehicle in the case of an accident.

Examples of preferred cushioning systems are shown in the inventor's other helmet-related patents, including U.S. Pat. Nos. 10,561,192; 8,955,169; 9,820,525; 10,980,306; and U.S. Published Patent Application Nos. 2020/0253314; 2019/029795; 2021/0045487; 2012/0198604; and 2015/0157082. The disclosures of these inventions are hereby incorporated by reference into this application.

The perimetral lip 33 that defines the front or face aperture 32 is sized and configured to matingly receive the perimetral edge 46 of the shield 19, in a manner that provides an effective dust barrier to thereby resist the intrusion of particulate matter, such as dust, that is exterior of the helmet, from passing through the barrier that is created and thereby intruding into the interior of the helmet adjacent to the user's eyes.

The seal is preferably capable of preventing, or severely restricting, the intrusion of particulate matter and moisture that is 10 microns or greater and, in a most preferred embodiment, is capable of preventing, or seriously restricting the intrusion of particulate matter that is seven microns or greater. In a most preferred embodiment, the barrier created between the engagement of the perimetral edge of the shield 19 and the perimetral lip 33 of the helmet 10 body 11 prevents, or significantly restricts the intrusion of particulate matter that is two microns or greater in size.

The sizes given above are typical sizes of particulate matter that might be encountered as "road dust" of the type that is stirred up and, becomes airborne on dry days, through the action of wind, and the movement of objects such as other vehicles on an unpaved road or trail surface.

Dust of this type is the type of particulate matter that a rider who is riding his motorcycle or ATV on dusty roads and off-road trails is most likely to encounter and, as such, is the type most likely to cause irritants to the user's eyes.

The perimetral lip 33 includes a top portion 86 that extends at the interface between the exterior brow of the helmet 10 and the aperture 32, and is generally arcuate in configuration to correspond to the arc of the front of the helmet. The perimetral lip 33 also includes a bottom portion 66 which extends along the chin portion 28 of the helmet at the interface between the jaw portions 24, 26 and chin portion 28 and the aperture 32.

Figure 21:
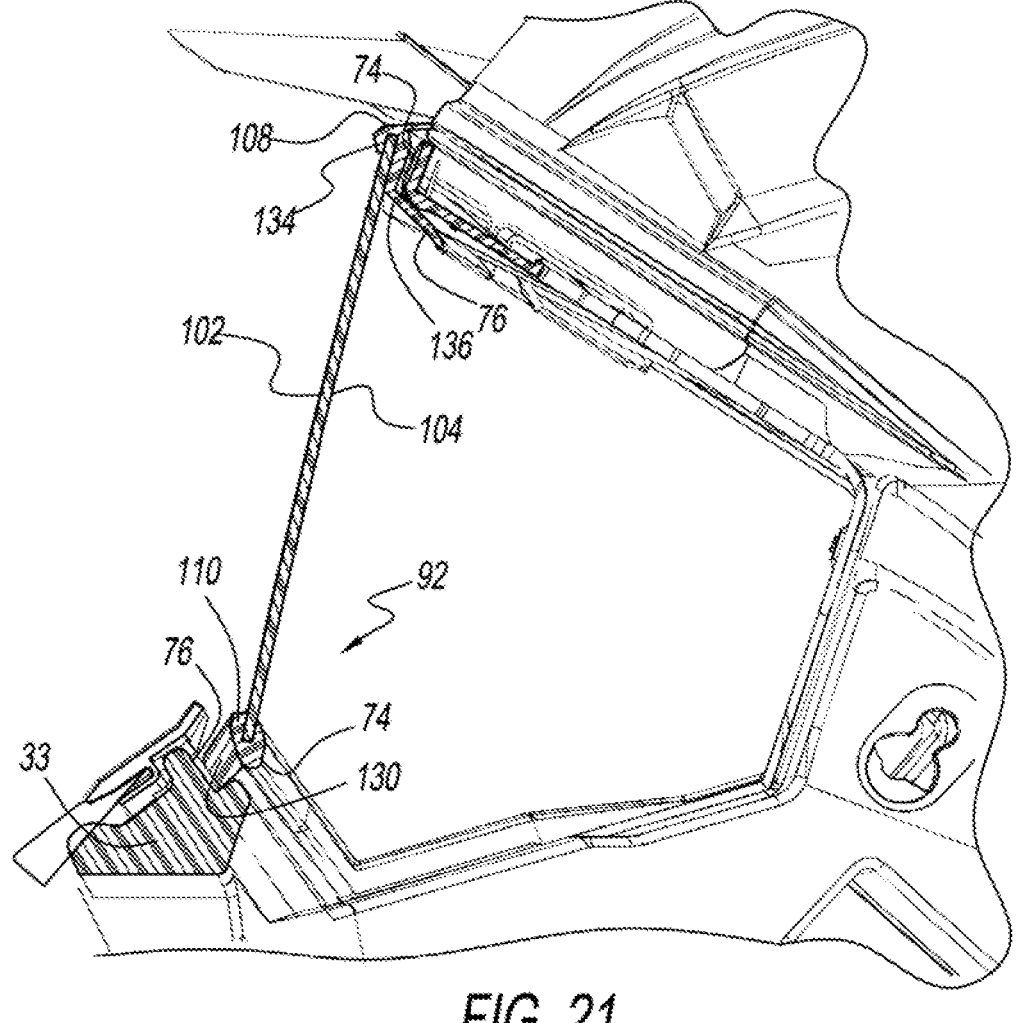
FIG. 21 is a sectional view taken along lines 20-20 of FIG. 17.

As best shown in FIG. 21, the perimetral lip 33 in the top portion 64 and bottom portion 66 is generally L-shaped to include a forwardly-facing surface 74 which is somewhat vertically disposed and a vertically-facing surface 76 which is somewhat horizontally disposed As will be described in more detail later, this results in a somewhat L-shaped cross-section, which is matingly engageable with a complementary configured L-shaped configuration in the shield sealing member.

The perimetral lip 33 also includes a first side portion 52 and a second side portion 53. The first and second side portions 52, 53 of the perimetral lip are generally planar, and include a series of bumps to enhance frictional engagement between the first and second side portions 52, 53 of the perimetral lip of the helmet 50 and the first and second side surfaces 50, 51 of the sealing member of the shield. An L-shaped cross-section of the side portions 52, 53 is not as necessary as along the top and bottom portions 64, 66, since the flow of air along the side portions 52, 53, and the rearwardly-opening nature of the sides of the shield 19, and of the covering of the shield 19 with the strap 54 will largely prevent dust from intruding, since the dust is generally not engaging the sealing member with the pressurized force caused by the wind exerting as much force against the membrane.

The first and second side surfaces 52, 53 of the perimetral lip 33 serve as shield-engaging seats upon which the sealing member of the shield 19 rests to help to form a particle-resistant barrier.

The bottom portion 66 of the perimetral lip includes three segments. These segments include a relatively planar first jaw segment 86, a relatively planar second jaw segment 90, and an arcuate nose or front segment 92. The segments take their shape from the generally corresponding shape of the helmet 10. The arcuate nose or front segment 92 takes its shape because the front surface of the helmet includes a relatively higher vertically-extending front portion to accommodate the chin vent 38 through which air can pass to enter the interior 13 of the helmet 19 adjacent to the user's nose.

The shield member is best shown in FIGS. 3-14 and 21. Generally, the shield member 19 includes a front surface 42, a rear surface 43, and a perimetral edge 46. The perimetral edge 46 is sized and configured for sealingly-engaging the perimetral lip 33 of the helmet 10 body 11.

The shield member 19 includes a top portion 47, a bottom portion 48, a first side portion 50, and a second side portion 51. A strap 54 includes a first end 56 that is coupled by a clip to the right side of the shield 19 and a second end 60 that is coupled by a second clip 61 to the second side of shield 19. The strap also includes a middle portion 62 that extends generally between the first end 56 and second end 60 of the strap 54. When in use, the middle portion 62 extends around the exterior of the helmet 19 and, in particular, around the rear surface portion 14 of the helmet to help secure the shield 19 onto the helmet. The middle portion includes an adjustment member 65 which includes a three-bar slide adjuster 67 and ring 69. The adjustment member 65 enables the user to adjust the length of the straps so that it fits onto the helmet to which the shield 19 is attached in the manner that holds the shield securely onto the helmet.

Since the shield 19 engages the helmet along the perimetral lip 33, pulling the strap extra tightly to make sure that it is secured onto the helmet 10 does not add additional pressure to the user's face. Rather, because of the inventive design of the present invention, the tightness of the strap 54 should have no measurable impact on the way that the helmet 10 feels to the user.

The general shape of the perimetral edge 46 of the shield member 19 conforms generally to the shape of the perimetral lip 33 of the helmet.

The top portion 47 of the perimetral edge 46 is generally arcuate, and is sized and configured to matingly engage the arcuate top portion 84 of the perimetral lip 33. Further, the bottom surface of the shield 48 includes three distinct segments, including a first jaw-engaging portion 48A, a second jaw-engaging portion 48B, and a nose or chin vent central portion 48C, These shapes are dictated largely to conform to the corresponding engagement surfaces of the relatively planar first jaw segment 86, the relatively planar second jaw segment 90, and the arcuate nose or front segment 92.

It will be appreciated that the shape and configuration of the perimetral edge 46 of the shield 19 would likely change if perimetral lip 33 would have a configuration different than that shown in the drawings. For example, the arcuate portion 48C of the bottom edge of the shield 46 might not be necessarily arcuate if the helmet with which the shield 19 was used did not include the chin or nose vent 38.

The shield 19 is comprised of three primary components, including the strap 54 and first 53 and second 61 clip assembly, a transparent lens 34 and a sealing member 53. The transparent lens includes an edge portion 106 that includes a top edge 108, a bottom edge 110, a first side edge 112, and a second side edge 114. The shapes and configurations of the edge portion 106 are generally similar to the configuration of the shield 19 as a whole.

The transparent lens 100 is preferably made to enable the user to look through the lens without losing any significant detail. Additionally, the lens 100, if colored, should still be transparent, and should be tinted at a color that will not significantly distort the colors that the user sees through the lens. In particular, the user should be able to look through the lens 100 and recognize the red of a red light, the green of a green light, and the yellow of a yellow light traffic signal.

Further, the lens 100 should be made from a relatively strong material. The most common material from which lenses 100 are made is polycarbonate, because of its toughness and shatter resistance. In the United States, many states require a lens 100 to meet or exceed the standards set forth in the Vehicle Equipment, Safety Commission Number 8 (VESC-8 or V-8) and Snell. The V-8 test requires that the shield be able to not allow lens 100 penetration if a 1.56 ounce steel projectile with a conical point strikes the shield at 20 miles per hour. The Snell test includes a pellet gun test that also prohibits the test projectile from entering the helmet.

The second component of the shield 19 is a sealing member 130. The sealing member 130 essentially comprises an elastomeric gasket type device that is coupled to and engages the perimetral edge of the lens 100. The sealing member 130 is preferably comprised of a deformable material such as a thermoplastic urethane material, or a thermoplastic elastomer material that has a durometer hardness of between of about 40 Shore A and 80 Shore A. Most preferably, the durometer hardness of the sealing member should be between about 60 Shore A and 70 Shore A.

The sealing member 130 preferably engages substantially all of the edge portion 106, of the lens 100 and may be molded in a manner so that the side portions of the sealing member are formed to either be a part of the clips 53, 61, or are formed to enable the clips 53, 61 to engage the sealing member 130 in a manner that securely engages the sealing member 130 to the clips 53, 61 and thereby the strap 54.

Preferably, the sealing member 130 engages the entire perimetral lip. However, this engagement of the entire perimetral lip may include portions that are near, but not at the edge 106. For example, near the side portions 50, 51 of the transparent lens 100, the sealing material may just extend on a planar surface of the transparent lens 100 so that the perimetral lip engaging surface of the sealing member 100 can better engage the generally planar first 52 and second 53 side portions of the perimetral lip 33.

The important feature is that the sealing member engages the perimetral lip 33 for preventing a significant quantity of particulate matter from entering the interior of the helmet through the forward-facing aperture of the helmet 10. The seal should be significantly complete, so that the particulate barrier created by the engagement of the sealing member 130 and perimetral lip 33 is capable of preventing the intrusion of particulate materials having a size of about 10 microns or greater.

More preferably, the barrier should be capable of resisting the intrusion of particulate materials that are about seven microns or greater and, most preferably, capable of resisting the intrusion of particulate materials having a size of about two microns or greater. The significance of these sizes is that they are the typical sizes of "road dust" particles of the type that are stirred up through either the action of wind, or other vehicles traveling along an unpaved road or trail of the type that an off-road rider would likely be driving his motorcycle, off-road bicycle, or ATV.

One configuration in which the sealing member can be manufactured, especially for those portions of the sealing member other than the side edge surfaces, is to have a sealing member 130 that includes a first portion 134 placeable against the front surface 102 of the lens 100, a second portion 136 that is placeable against the second or interior surface 104 of the lens 100, and a third portion 138 that includes a groove 140 for receiving the perimetral lens edge portion 106. In this configuration, the sealing member 130 is configured for matingly engaging the perimetral lip 33 of the helmet 10 to create a particulate barrier capable of preventing a large portion of typical road dust particulates from passing through the barrier.

Figure 19:
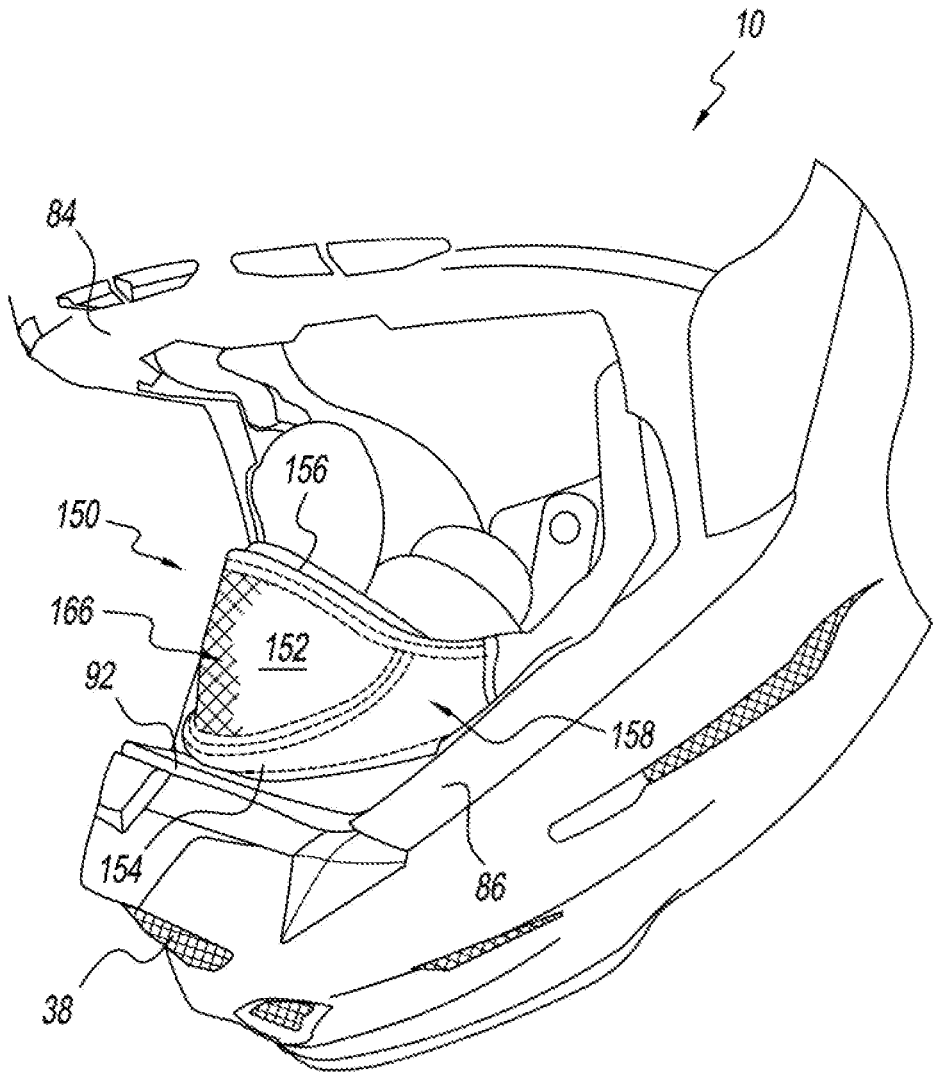
FIG. 19 is a perspective view of the helmet of the present invention showing the optional breath box.
Figure 20:
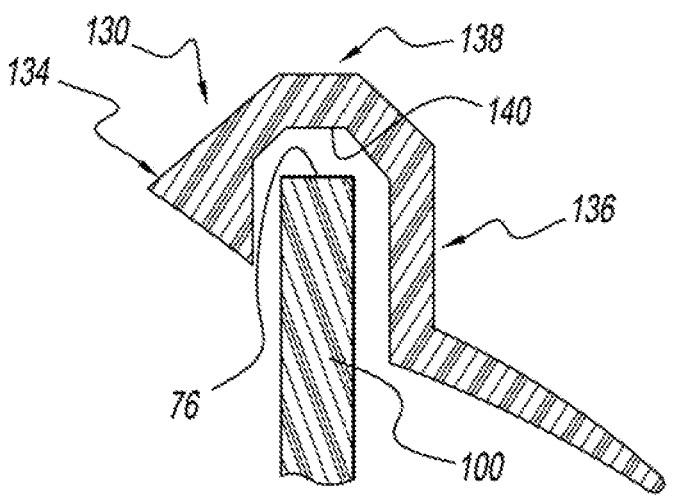
FIG. 20 is an enlarged, sectional, exploded view of the sealing member and top edge of the transparent lens.

Turning now to FIG. 19 a helmet 10 is shown that includes a breath box 150. The purpose of a breath box 150 is to create a barrier that restricts the movement of particulate matter and air between a lower space of the interior of the helmet that is adjacent to the user's nose and mouth, and an upper area of the interior of the helmet 10 that is adjacent to the user's eyes.

One of the benefits of a breath box 150 is that it prevents moisture, such as that found in exhaled breath from engaging the interior surface 104 of the transparent lens 100 to thereby help to prevent the interior surface 104 of the lens 100 from getting fogged up, such as might occur in humid situations, or situations wherein the helmet goes from a relatively cold area to a relatively warmer area.

Just as the breath box helps to prevent the passage of humid air to the interior of the helmet 10 adjacent to the user's eyes, it also helps to restrict the flow of dust to the area adjacent to the eyes.

As discussed above, there should not be a significant amount of dust that enters the interior space of the helmet adjacent to the user's mouth and nose through either the jaw vents 40 or the chin vent 38 as the jaw vent 40 and chin vent 38 preferably both include filters for trapping the dust. However, dust will enter the interior of the helmet around the base edge 36 of the helmet 10.

The breath box 150 includes an exteriorly-facing surface 152 and an interiorly-facing surface (not shown). The breath box 150 further includes a forward edge 154 that can include an attachment material for attaching the forward edge to the interior surface of the helmet, to help create a barrier to the passage of air and particulate matter around the forward edge 154 of the breath box 150. The breath box includes a rearward edge 156 that is configured for engaging the nose and face of the user to form a barrier between the area of the interior of the helmet below the breath box 150 and the area, of the interior above the breath box 150, which is the area of the interior of the helmet that is adjacent to the eyes of the user.

The breath box further includes a first side portion 158 and a second side portion 162 that are relatively smaller and have a lower height than the relatively enlarged central portion 166. The first and second side portions can include a fastener such as a hook and loop type fastener that is disposed on the exteriorly-facing surface 152 of the breath box 150 and may be engageable with a complementary hook and loop fastener that is disposed on the interior surface of the helmet.

Figures 5, 6:
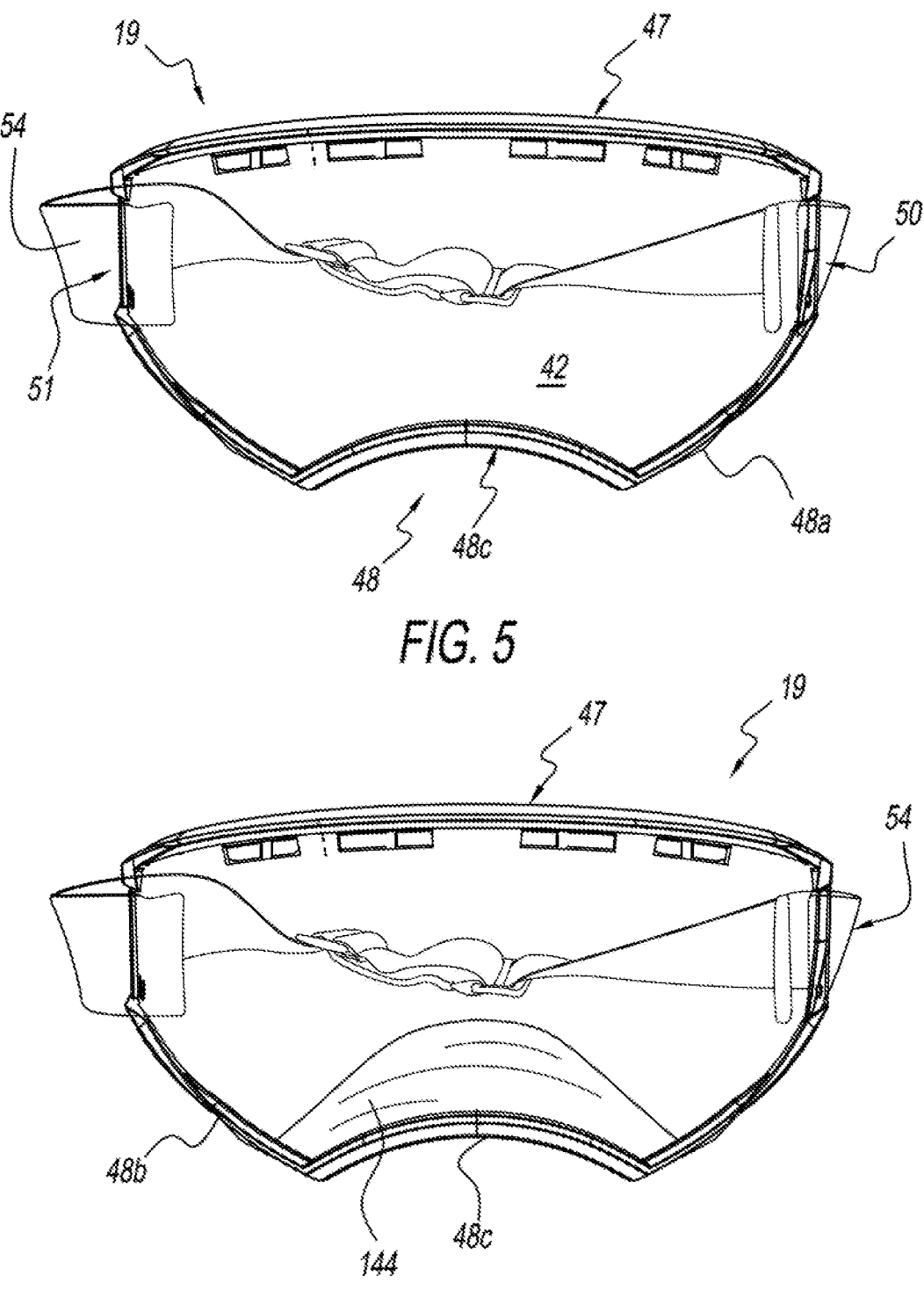
FIG. 5 is a front view of the shield of the present invention.
FIG. 6 is a front view of the shield member of the present invention, showing the nose gasket attached thereto.
Figures 7, 8:
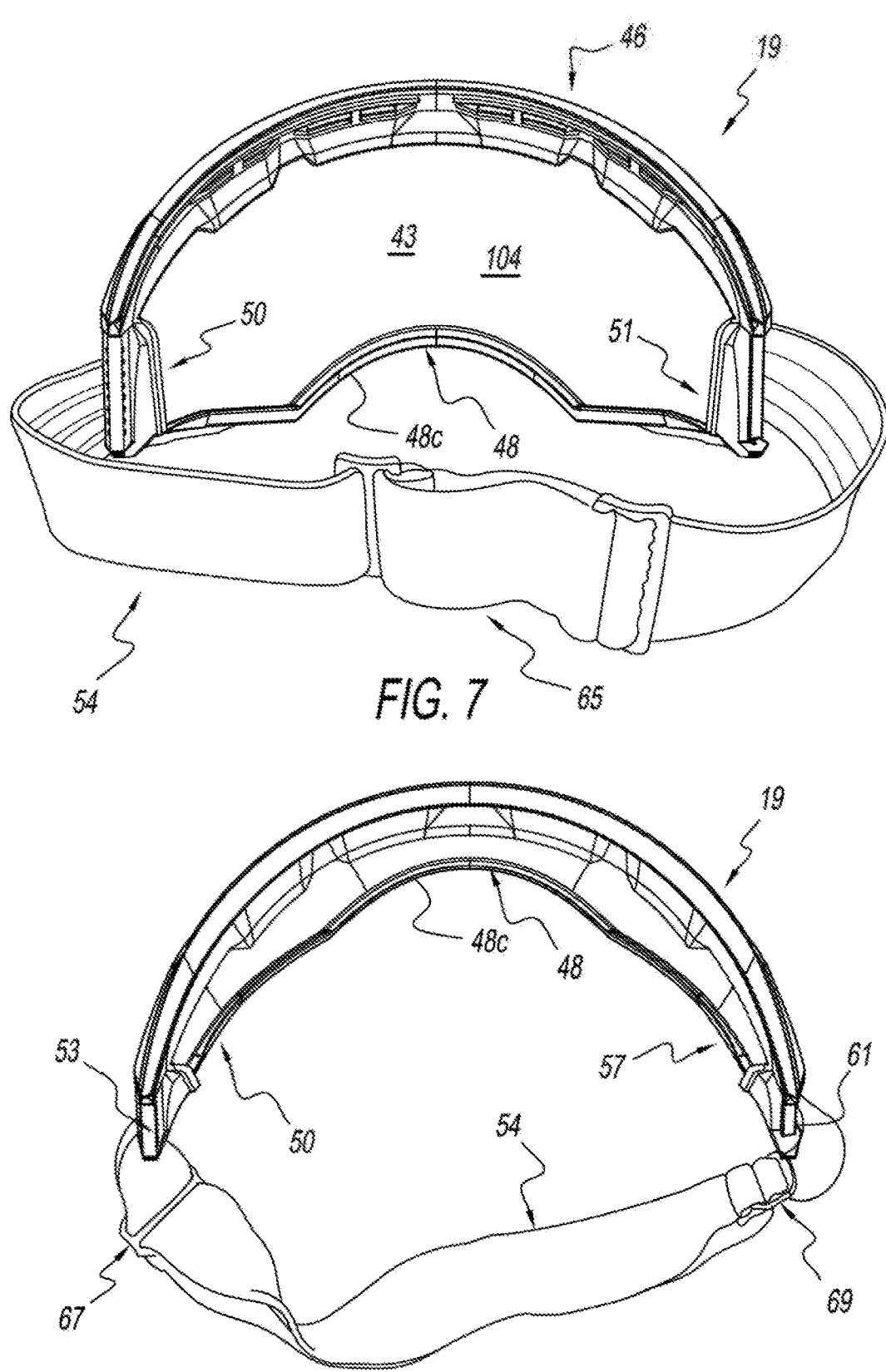
FIG. 7 is a rear view of the shield member of the present invention.
FIG. 8 is a top view of the shield of the present invention.
Figure 9:
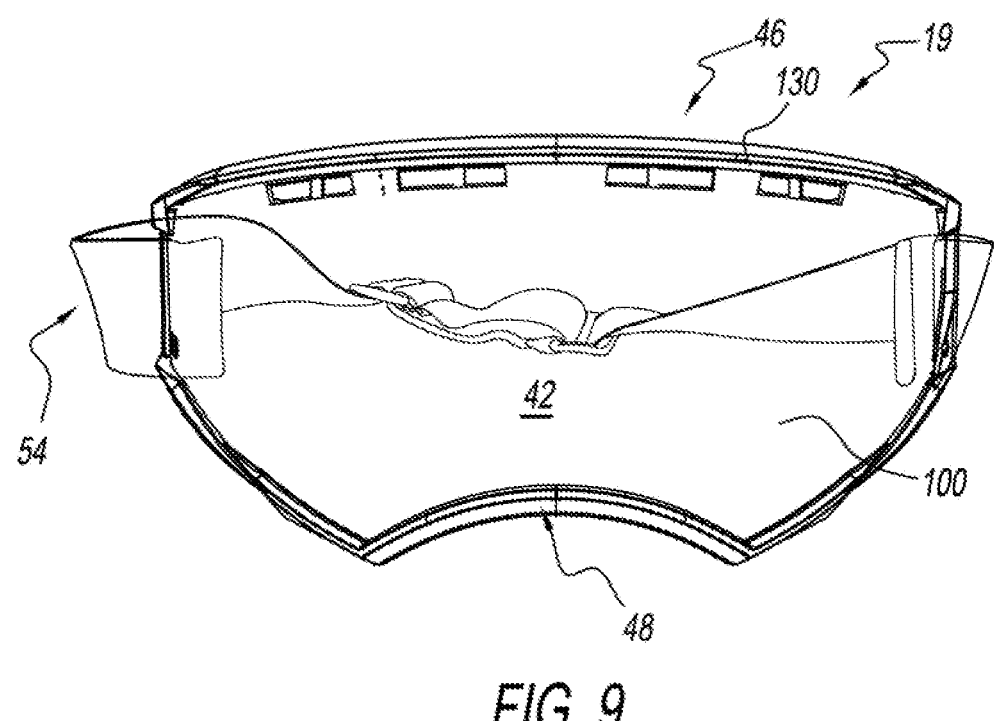
FIG. 9 is another front view of the of the shield of the present invention.
Figure 10:
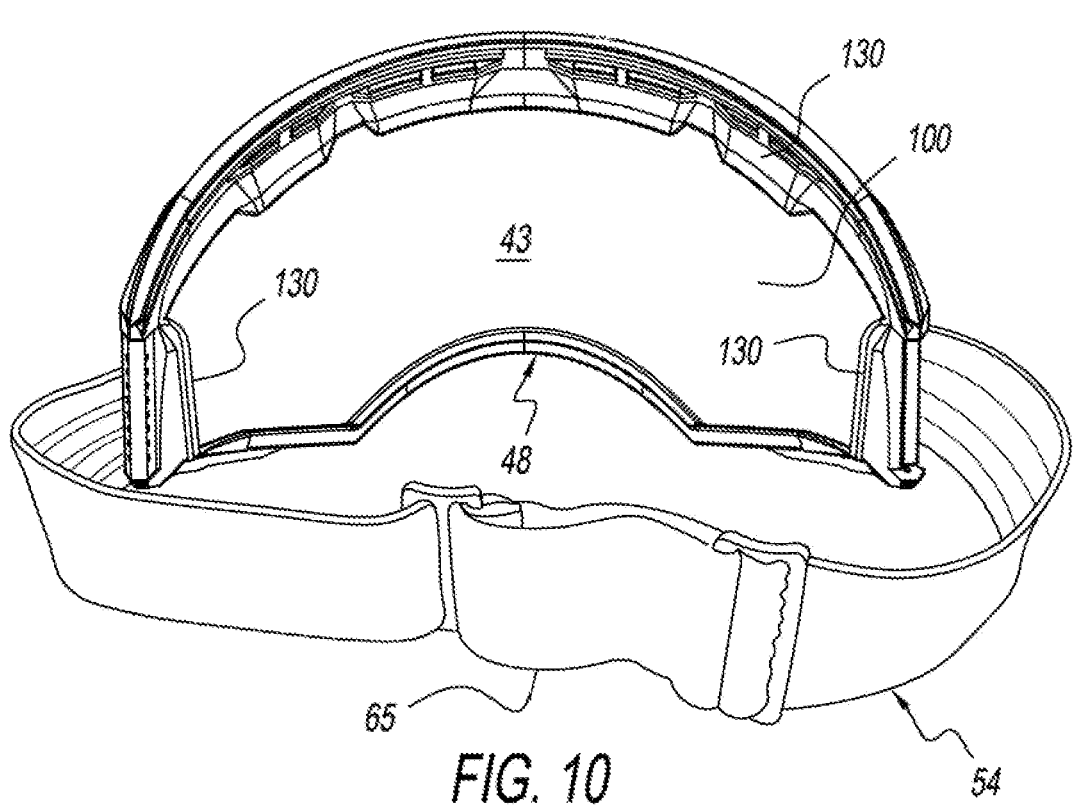
FIG. 10 is a rear view of the present invention showing the inside surface of the shield.
Figures 11, 12:
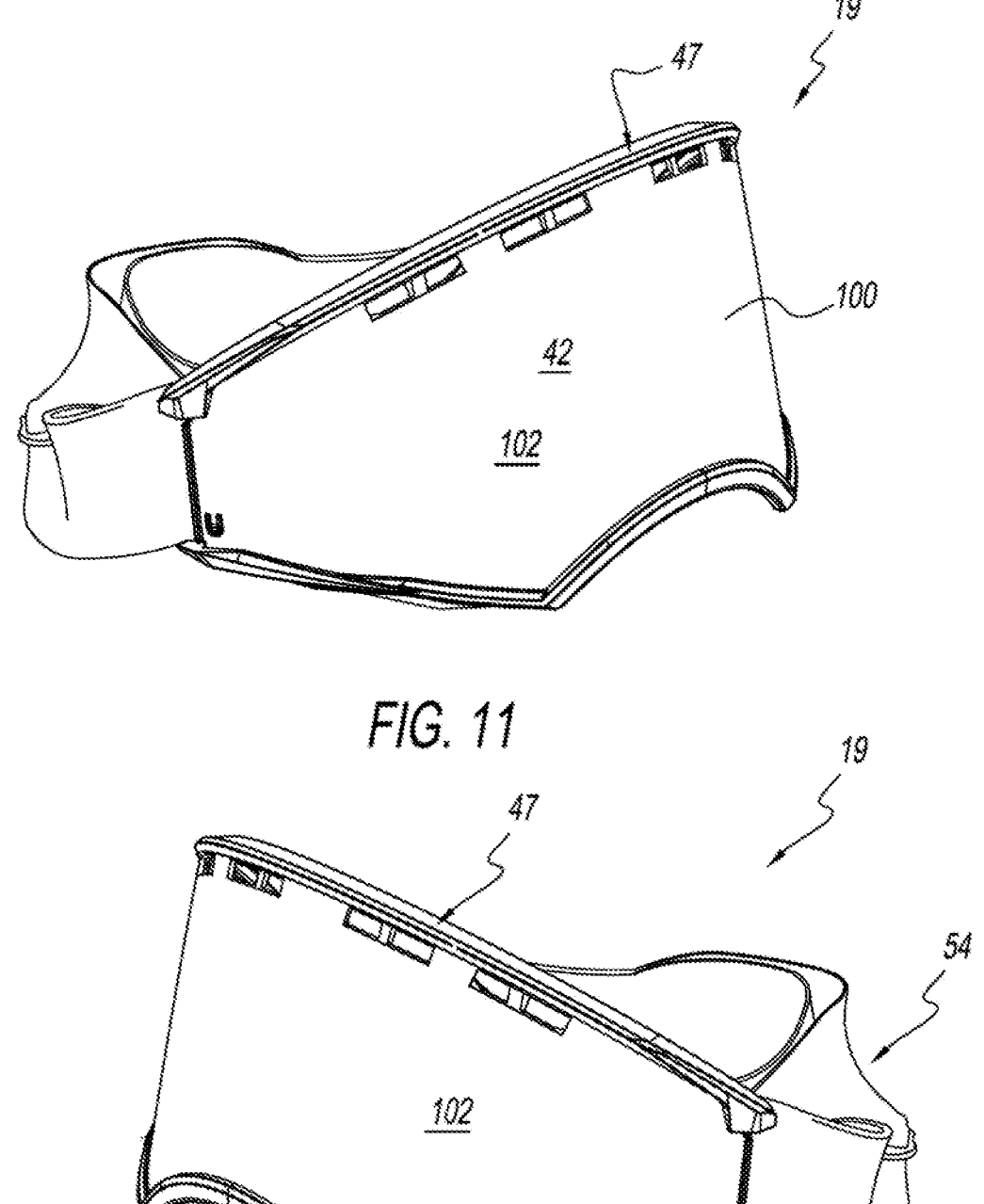
FIG. 11 is a right side perspective view of the shield of the present invention, showing the front, or outside surface, of the shield.
FIG. 12 is a left side perspective view of the shield of the present invention.
Figure 13:
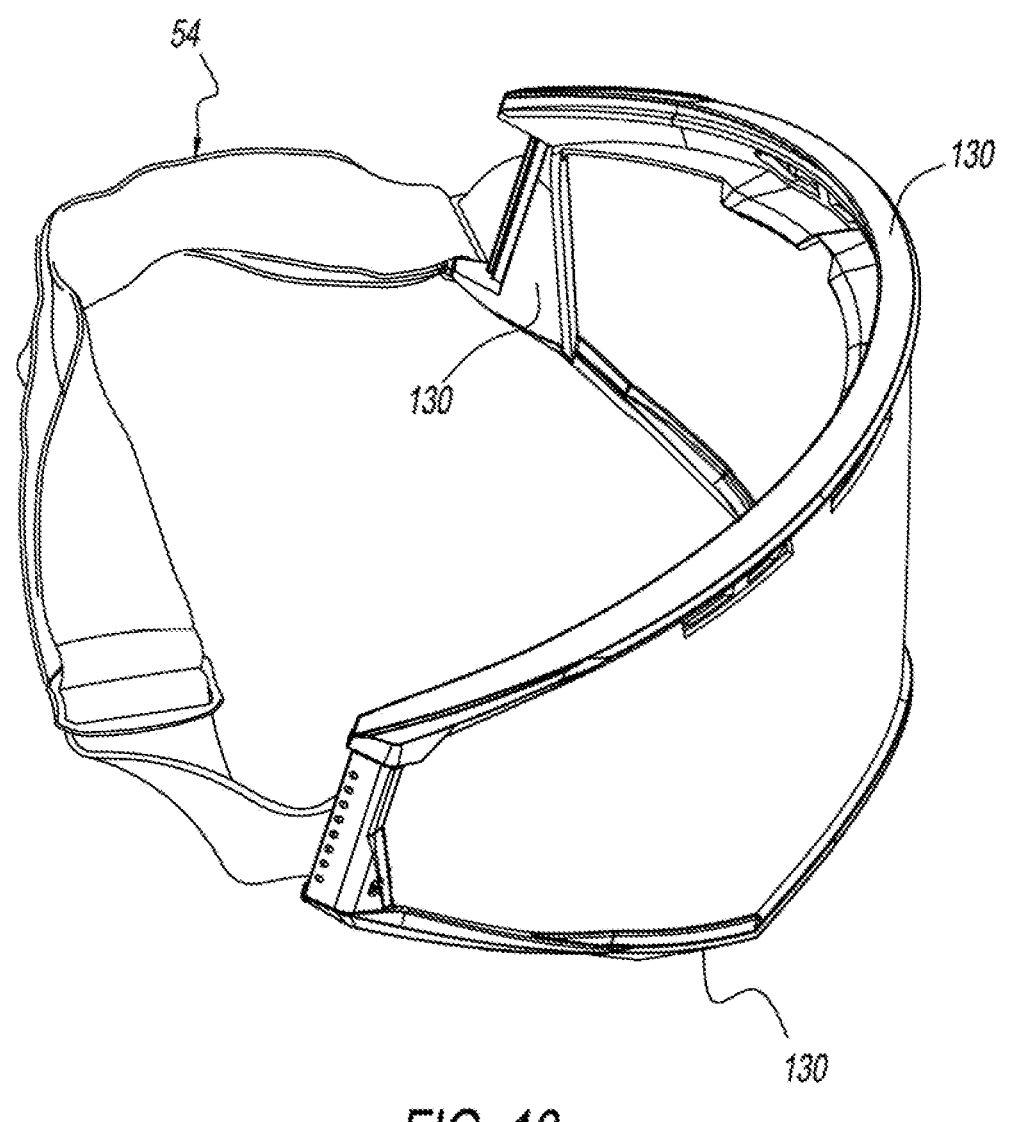
FIG. 13 is perspective, right side view of the shield of the present invention.
Figure 14:
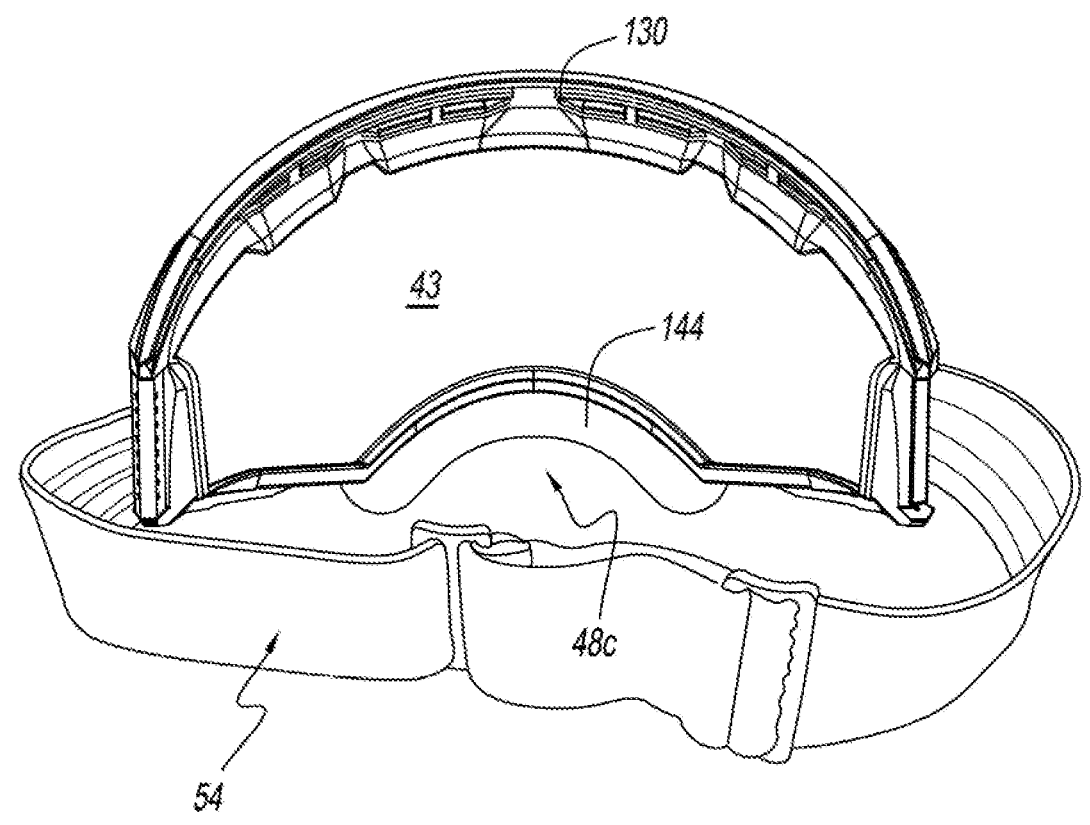
FIG. 14 is a front view of the shield of the present invention attached to a motorcycle helmet such as the helmet of FIG. 1
Figure 15:
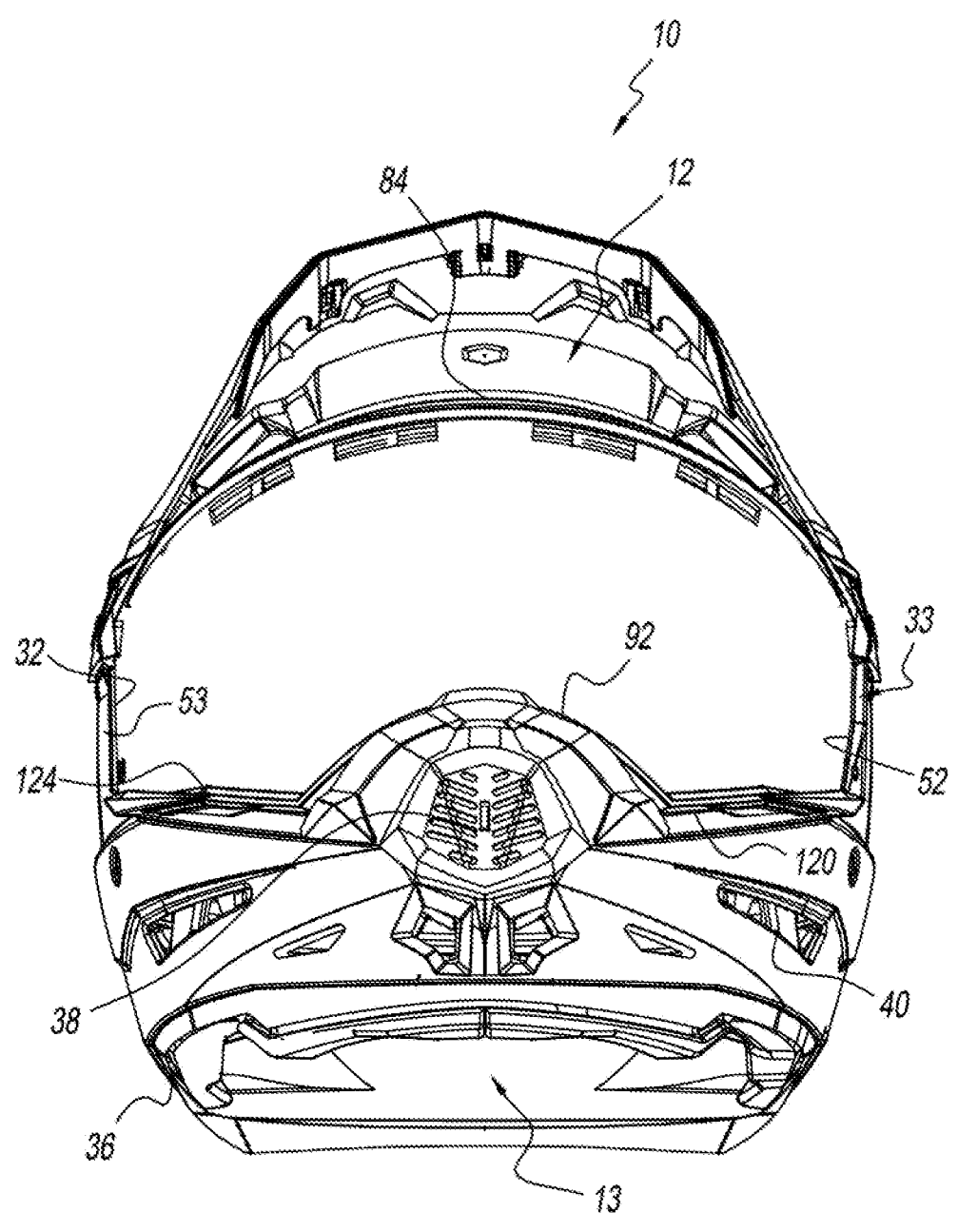
FIG. 15 is front side perspective view of the shield of the present invention attached to, or positioned on a helmet.
Figure 16:
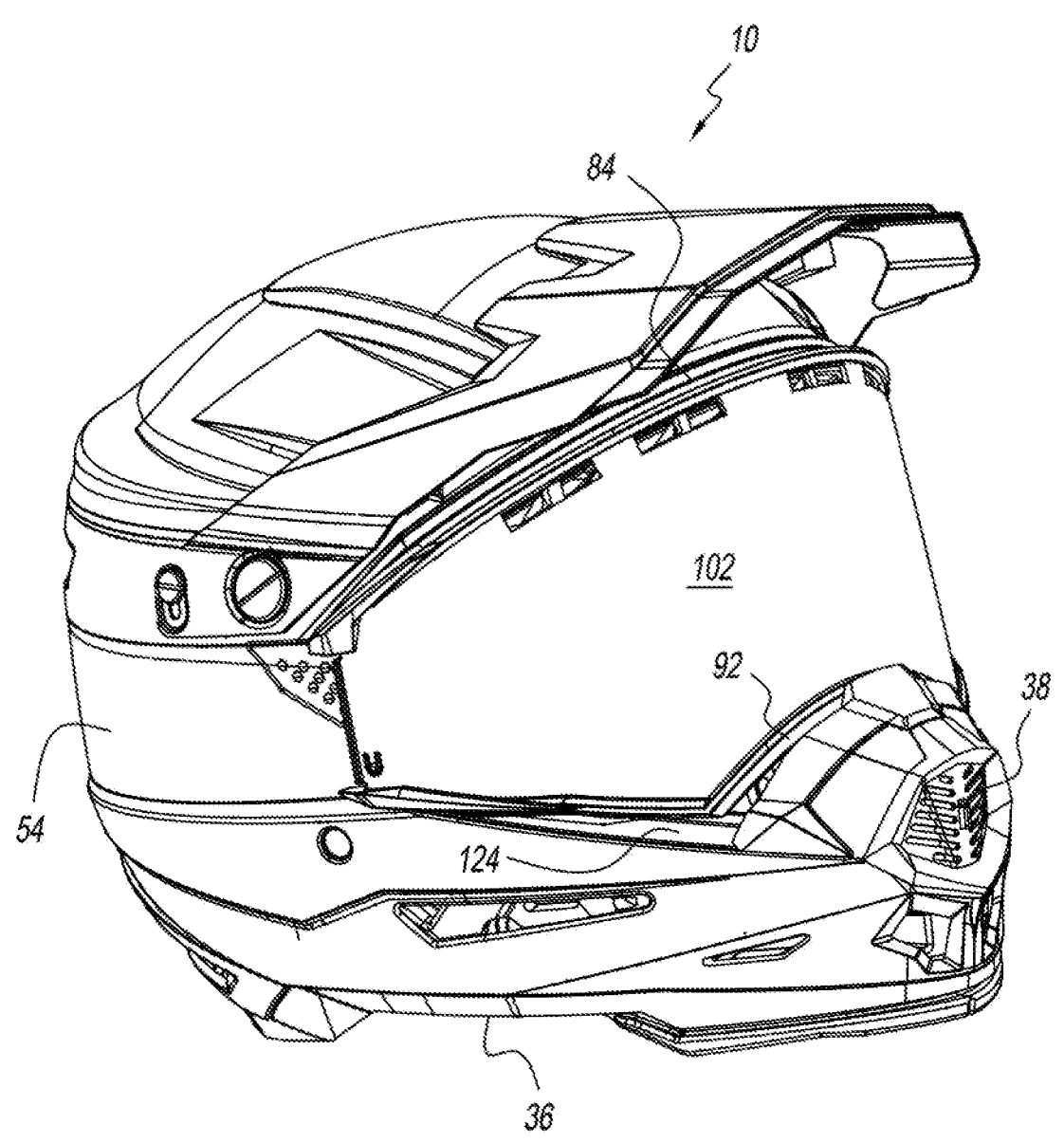
FIG. 16 is a right side perspective view of the shield of the present invention.
Figure 17:
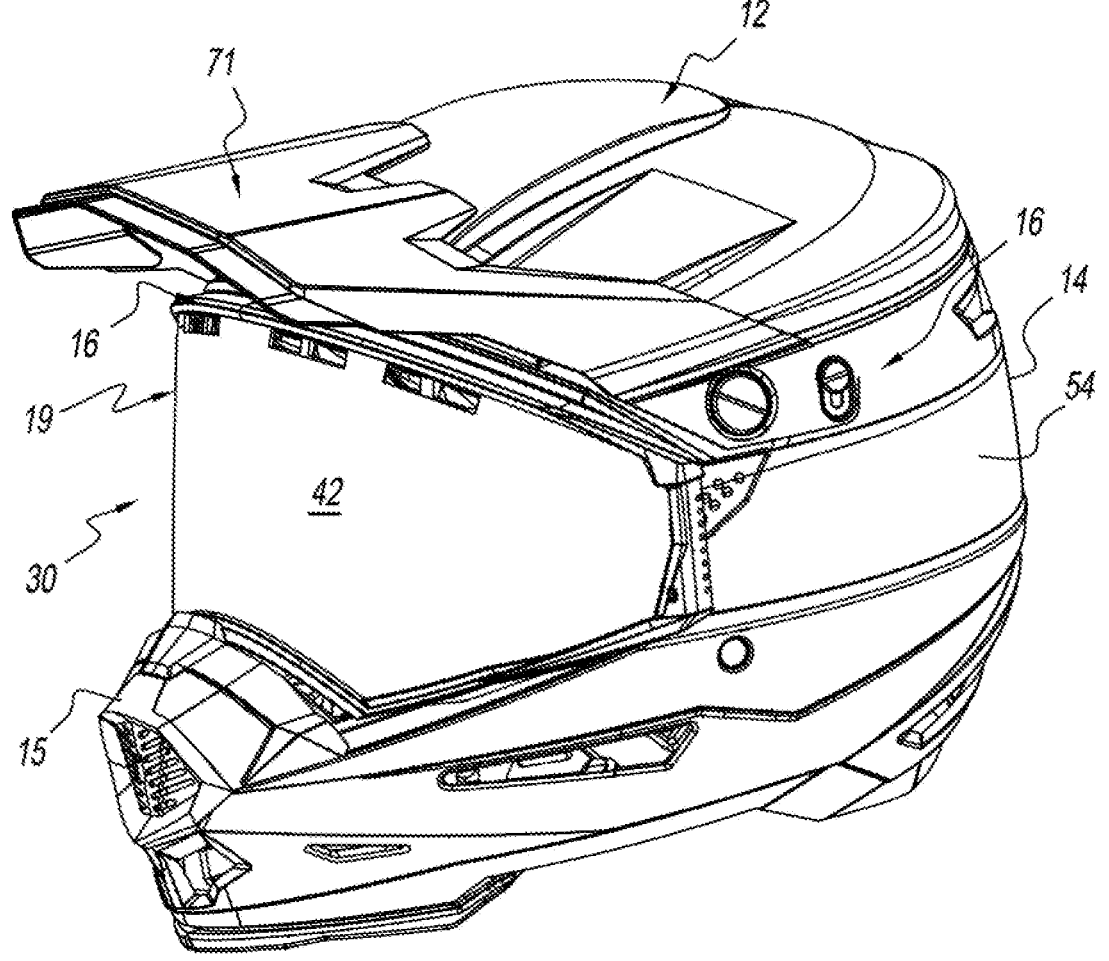
FIG. 17 is a left side view of the goggle-shield of the present, invention coupled to a helmet in the use position.
Figure 18:
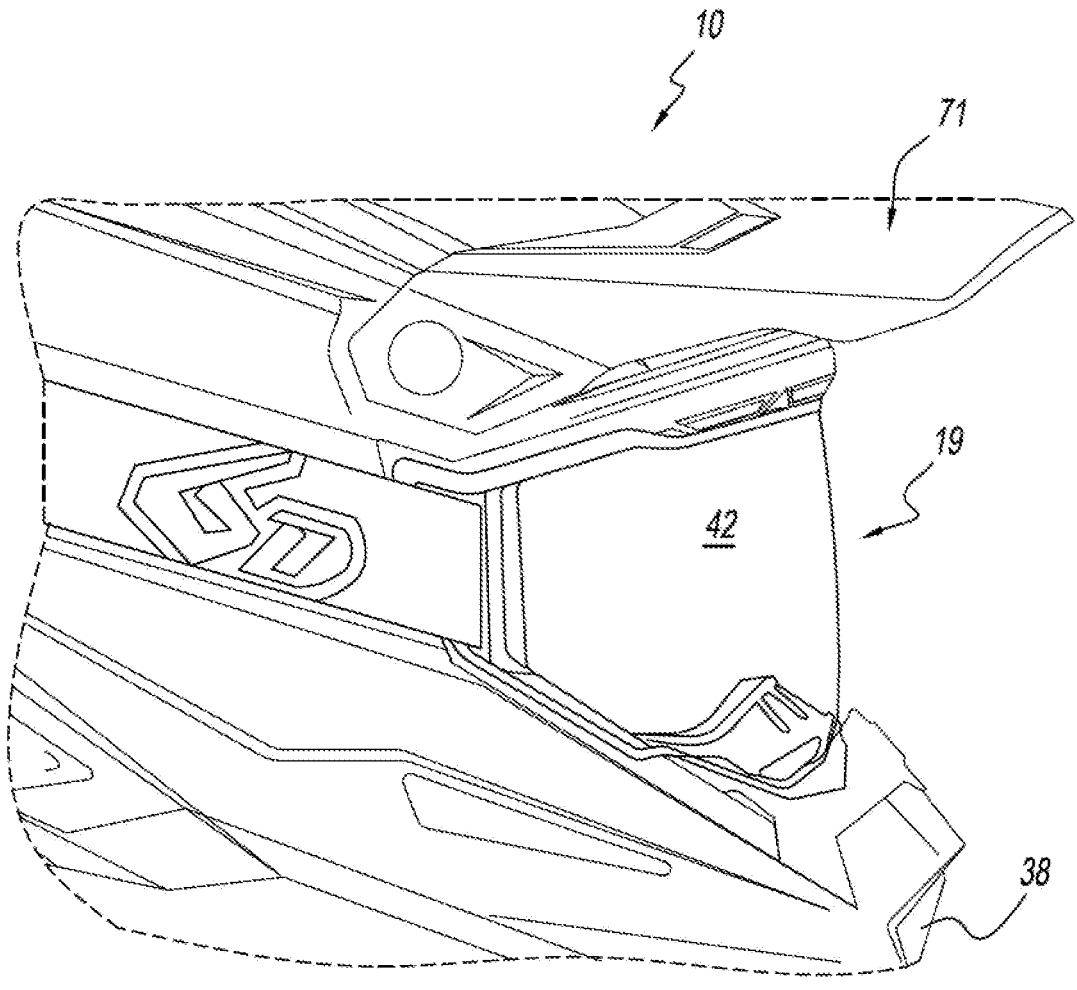
FIG. 18 is a right side view of the goggle-shield-helmet of the present invention, containing annotations directed to features of the invention.

In some embodiments, the helmet goggle may employ a nose gasket (FIG. 6). A nose gasket 144 is a gasket that is generally fitted onto the exterior frontal surface of the shield 19 to accurately engage the shield 19 onto the outer surface of the helmet shell at the nose vent area 15, and may comprise a rubber or foam material similarly defined as the goggle sealing member 130. The nose gasket 144 is best shown at FIG. 14, as being coupled to the shield 19, adjacent to arcuate portion 48C of the shield.

Having described the invention in detail with references to preferred embodiments, it will be appreciated that the above-described invention is not limited by the description herein, but rather, shall be limited only by the claims and their equivalents that shall be attached hereto.

What is claimed is:

1. A protective helmet comprising:
    a head receiving helmet body including a head receiving interior and an exterior, wherein the exterior has, a crown portion, a brow portion extending downwardly from the crown portion, a rear portion, two opposing side portions, and a chin bar, wherein the crown portion, the brow portion, the rear portion, the chin bar, and the opposing side portions are a unitary assembly configured to provide impact protection for motorsports and cycling;
    a perimetral lip defining a forward-facing aperture in a front surface of the head receiving helmet body, wherein the perimetral lip extends along the brow portion, the opposing side portions, and the chin bar, wherein the perimetral lip includes a shield member engaging surface;
    a transparent shield member engageable with the head receiving helmet body and configured to be placeable adjacent to the forward-facing aperture in the front surface of the head receiving helmet body, the transparent shield member including a front surface, a rear surface, and a perimetral edge, wherein the perimetral edge has a top portion, a bottom portion, a first side portion and a second side portion, the perimetral edge being sized and configured for engaging the perimetral lip of the head receiving helmet body at the brow portion, the opposing side portions, and a portion of the chin bar;
    an elastomeric sealing member extending about the perimetral edge of the transparent shield member and configured to provide sealing engagement between the perimetral edge of the transparent shield member and the shield member engaging surface of the perimetral lip of the helmet body; and
    a strap having a first end, a second end, and a middle portion extending between the first and second ends, wherein the first end is coupled to the first side portion of the transparent shield member, the second end is coupled to the second side portion of the transparent shield member, and the middle portion is configured to engage the rear portion of the head receiving helmet body, and wherein the engagement of the perimetral edge of the transparent shield member with the perimetral lip of the helmet body enables an increasing force exerted against the transparent shield member to be exerted against the protective helmet rather than directly against a user's face.

2. The protective helmet of claim 1, wherein the elastomeric sealing member includes a helmet engaging portion coupled to the rear surface of the transparent shield member.

3. The protective helmet of claim 1, wherein the elastomeric sealing member is coupled to the head receiving protective helmet body and is sealingly engageable with the rear surface of the transparent shield member.

4. The protective helmet of claim 1, wherein the elastomeric sealing member is coupled to the perimetral edge of the transparent shield member, the elastomeric sealing member including a surface engageable with the perimetral lip for providing a particulate resistance seal between the transparent shield member and the perimetral lip.

5. The protective helmet of claim 4, wherein the transparent shield member includes a transparent lens having a perimetral lens edge, the elastomeric sealing member includes a first portion placeable around the front surface of the transparent shield member, a second portion placeable against the rear surface of the transparent shield member, and a groove disposed between the first and second portions and being sized and configured for receiving the perimetral lens edge.

6. The protective helmet of claim 4, wherein the transparent shield member includes a lens portion having a perimetral lens edge, a front lens surface and a rear lens surface, and the elastomeric sealing member is coupled to the perimetral lens edge.

7. The protective helmet of claim 6, wherein the perimetral lens edge includes an upper lens edge portion, a lower lens edge portion, a first side lens edge portion and a second side lens edge portion wherein the elastomeric sealing member engages each of the upper lens edge portion, the lower lens edge portion, the first side lens edge portion and the second side lens edge portion.

8. The protective helmet of claim 7, wherein the elastomeric sealing member engages all of the perimetral edge, and engages a first side portion of the protective helmet and a second side portion of the protective helmet along a planar portion of the first side and the second side portions of the protective helmet.

9. The protective helmet of claim 7, wherein the elastomeric sealing member engages the perimetral lip configured for preventing a significant quantity of particulate matter from entering the head receiving interior of the protective helmet through the forward-facing aperture.

10. The protective helmet of claim 6, wherein the elastomeric sealing member includes a perimetral lip engaging portion comprised of a deformable material having a durometer hardness of between 40 Shore A and 80 Shore A.

11. The protective helmet of claim 6, wherein the elastomeric sealing member includes a perimetral lip engaging portion comprised of at least one of the thermoplastic urethane material and a thermoplastic elastomer material, the material having a durometer hardness of between 60 Shore A and 70 Shore A.

12. The protective helmet of claim 4, further comprising:
a removable breath box configured to be disposed adjacent to a mouth of the user and a nose of the user, and wherein the removable breath box is configured for restricting air in the helmet adjacent to the mouth of the user and the-nose of the user from entering an area of the protective helmet adjacent to the user's eyes.

13. The protective helmet of claim 1, further comprising:
a removable breath box configured to be disposed adjacent to a mouth of the user and a nose of the user, and wherein the removable breath box is configured to prevent air in the protective helmet adjacent to the mouth of the user and the nose of the user from entering an area of the protective helmet adjacent to the user's eyes.

14. The protective helmet of claim 13, wherein the removable breath box comprises a deformable member having a forward edge coupled to the protective helmet, and a rearward edge configured for engaging the nose and face of the user to form a barrier between the area of the head receiving interior of the protective helmet below the removable breath box and the area of the head receiving interior above the removable breath box.

15. The protective helmet of claim 1, further comprising a clip member coupled to the strap and configured for being engageable with the transparent shield member for removably coupling the strap to the shield member.

16. The protective helmet of claim 1, wherein the transparent shield member comprises a transparent lens portion having a perimetral edge and an elastomeric sealing member coupled to the perimetral edge of the transparent lens portion, the elastomeric sealing member including a protective helmet engaging portion disposed on the rear surface, the protective helmet engaging portion being sized and configured for mating with the perimetral lip of the protective helmet to create a particulate barrier.

17. The protective helmet of claim 16, wherein the particulate barrier is capable of resisting the intrusion of particulate materials having a size of 10 microns or greater.

18. The protective helmet of claim 16, wherein the perimetral edge includes an upper lens edge, a lower lens edge, a first side lens edge and a second side lens edge, and wherein the elastomeric sealing member engages each of the upper lens edge, the lower lens edge, the first side lens edge and the second side lens edge.

19. The protective helmet of claim 18, wherein the elastomeric sealing member further includes: a first portion placeable against a front lens surface; a second portion placeable against a rear lens surface; a third portion including a groove for receiving the perimetral lens edge; and wherein the elastomeric sealing member is configured for matingly engaging the perimetral lip of the helmet to create a particulate barrier between an internal eyeport area of the helmet and the external environment surrounding the helmet and capable of preventing ten micron or greater sized particulate matter from passing through the particulate barrier.

20. The protective helmet of claim 18, wherein the elastomeric sealing member is comprised of a deformable material having a durometer hardness of between 40 Shore A and 80 Shore A.

21. A shield for use with a protective motor sport or cycling helmet, the protective motor sport or cycling helmet including a helmet body with a head receiving interior, an exterior having a front surface configured to extend from a user's forehead to a user's chin, a rear surface, and a perimetral lip defining a forward-facing aperture in the front surface of the helmet body, the perimetral lip including an outwardly facing shield engagement surface, the shield comprising:
a transparent shield member engageable with the helmet body and configured to be placeable adjacent to the forward-facing aperture of the helmet body, wherein the transparent shield member includes a front surface, a rear surface, and a perimetral edge, wherein the perimetral edge has a top portion, a bottom portion, a first side portion and a second side portion, and wherein the perimetral edge is configured for engaging the perimetral lip of the helmet body;
an elastomeric sealing member extending about the perimetral edge of the transparent shield member and configured to sealingly engage with the outwardly facing shield engagement surface of the perimetral lip of the helmet body, the transparent shield member and a user's face to reduce intrusion of particulates into an area adjacent to a user's eyes;
wherein the transparent shield and the elastomeric sealing member fail to contact a user's face, wherein force applied to the transparent shield member is transferred to the perimetral lip of the helmet body; and
a strap having a first end, a second end, and a middle portion extending between the first end and the second end, wherein the first end is coupled to the first side portion of the transparent shield member, the second end is coupled to the second side portion of the transparent shield member, and the middle portion is configured to engage the rear surface of the helmet body.

22. The shield of claim 21, wherein the elastomeric sealing member includes a helmet engaging portion disposed on the rear surface of the transparent shield member, the helmet engaging portion being sized and configured for mating with the perimetral lip of the helmet to create a particulate barrier.

23. The shield of claim 22, wherein the perimetral edge includes an upper edge, a lower edge, a first side edge and a second side lens edge, and wherein the elastomeric sealing member engages each of the lower edge, upper edge, first side edge, and second side edge.

\* \* \* \* \*